United States Patent [19]
Crocker

[11] Patent Number: 6,095,580
[45] Date of Patent: Aug. 1, 2000

[54] METHOD AND APPARATUS FOR AIDING THE HANDICAPPED IN PLACING AND RETRIEVING ITEMS

[76] Inventor: Susan Crocker, 11068 Sunnydale Ave., Englewood, Fla. 34224

[21] Appl. No.: 09/392,365

[22] Filed: Sep. 8, 1999

[51] Int. Cl.[7] ............................................. B25J 1/04
[52] U.S. Cl. ........................ 294/19.1; 294/1.1; 294/22
[58] Field of Search ............................ 294/1.1, 19.1, 294/22, 23, 24, 31.2, 138, 149, 150, 157; 40/316, 586, 617, 642.01; 248/317, 339, 340

[56] References Cited

U.S. PATENT DOCUMENTS

| | | | |
|---|---|---|---|
| 366,369 | 7/1887 | Bierman | 294/23 |
| 1,716,232 | 6/1929 | Kantor | 294/22 X |
| 2,989,334 | 6/1961 | Browne | 294/19.1 X |
| 3,561,718 | 2/1971 | Iverson | 294/19.1 X |
| 4,153,286 | 5/1979 | Piper et al. | 294/19.1 |
| 4,231,603 | 11/1980 | van Zelm | 294/19.1 |
| 4,249,763 | 2/1981 | Provencher et al. | 294/19.1 |
| 4,613,179 | 9/1986 | van Zelm | 294/19.1 |
| 4,711,482 | 12/1987 | Brown et al. | 294/19.1 |
| 4,758,035 | 7/1988 | Shimasaki | 294/19.1 |
| 4,993,766 | 2/1991 | Sutherland | 294/19.1 |
| 5,314,221 | 5/1994 | Hammer | 294/19.1 |
| 5,647,622 | 7/1997 | Schectman | 294/19.1 |

Primary Examiner—Johnny D. Cherry
Attorney, Agent, or Firm—John D. Gugliotta

[57] ABSTRACT

This invention is a device to aid the disabled in placing and retrieving items from hard to reach places in a kitchen. Specifically, it aids in placing and retrieving frozen foods off a top shelf of a freezer. The device wraps around freezer containers and uses a string and hook on the inside of a freezer to pull the item into and out of the freezer. The rubber hooks are attached to the freezer on the top edge. The rubber holder wraps around a container and a string attaches to the container and loops around the hook. The free end of the string is then used to raise and lower the food item to the handicapped person. A tag located on the free end of the string identifies the particular food item.

6 Claims, 4 Drawing Sheets

METHOD AND APPARATUS FOR AIDING THE HANDICAPPED IN PLACING AND RETRIEVING ITEMS

RELATED APPLICATIONS

The present invention was first described in Disclosure Document Number 451654 filed on Feb. 22, 1999. There are no previously filed, nor currently any co-pending applications, anywhere in the world.

BACKGROUND OF THE INVENTION

1. Field of the Invention

The present invention relates generally to kitchen aids and, more particularly, to a method and apparatus for aiding the handicapped in placing and retrieving items from kitchen cabinets or the freezer shelf.

2. Description of the Related Art

Handicapped people face obstacles on a daily basis that most of us take for granted. Simple tasks that are usually performed without thought require a great deal of effort and forethought on their part. Fortunately, the public is becoming increasingly aware of the difficulties that these people face and are responding in a positive manner. For example, legislation such as the Americans with Disabilities Act imposes responsibilities upon the public sector to make provisions to accommodate the physically handicapped so that they may gain access to, and take advantage of, the various goods and services available to others. Unfortunately, however, disabled people face many difficulties inside of their own home. One prime example is that the location of the freezer compartment above a refrigerator, places it just out of reach for many disabled persons, especially when they are trying to find a particular food product inside. The closeness of all the items, coupled with the lack of light and the difficulty in moving objects around make finding a desired item difficult even for the non-disabled. Accordingly, there is a need for a means by which handicapped individuals can easily remove frozen food products from the top shelf of freezers. The development of the Assist Handicapped People fulfills this need.

In the related art, there exist many patents for devices to aid a person, particularly the handicapped, in reaching objects at a distance. Typically, such devices consist of an elongated arm with a gripping means at one end, and at the other, a trigger for causing the articulating jaws of the gripping means to grasp an object. These devices may be purely mechanical in nature or powered by electric motors or batteries. The present invention is not one of these devices. It is a system whereby a handicapped person can retrieve and store food items in the freezer which is normally out of reach to such a person. It consists of a system for securing and hanging a food item on a hook in the freezer where it may be placed or retrieved via a rod member equipped with a hook on the end for lifting and carrying the food item to and from the freezer. Nothing in the prior art even resembles such a system and the apparatus just described.

A search of the prior art did not disclose any patents that read directly on the claims of the instant invention; however, the following references were considered related:

| U.S. Pat. No. | Inventor | Issue Date |
|---|---|---|
| 5,647,622 | Schectman | July 15, 1997 |
| 4,993,766 | Sutherland | Feb. 19, 1991 |
| 4,758,035 | Shimasaki | July 19, 1988 |
| 4,711,482 | Brown et al. | December 8, 1987 |
| 4,613,179 | van Zelm | Sep. 23,1986 |
| 4,231,603 | van Zelm | Nov. 4, 1980 |
| 5,314,221 | Hammer | May 24, 1994 |
| 2,989,334 | Browne | June 20, 1961 |
| 5,728,121 | Bimbo et al. | Mar. 17, 1998 |

SUMMARY OF THE INVENTION

It is therefore an object of the present invention to provide a system and apparatus to allow the handicapped to grasp and transfer a food item to and from the freezer.

It is another object of the present invention to work with prepackaged or self packaged frozen foods.

It is yet another object of the present invention to secure a food package with rubber straps.

It is yet still another object of the present invention to fasten the storage hooks to the freezer compartment with adhesive.

It is an advantage of the present invention that it works with any freezer.

It is another advantage of the present invention that it allows spacing of the food items by the user.

Briefly described according to one embodiment of the present invention, the method and apparatus to aid the handicapped in placing and retrieving items, as its name implies, is a method and apparatus that aids handicapped individuals in removing frozen food products from the top shelves of freezer compartments. Hook assemblies are attached to the inside portion of the freezer compartment using adhesive rated for the temperature and moisture environment that would be encountered inside of a freezer. Next, rubberized handling straps are secured around the frozen food product and secured in an "X" configuration using special tabs embedded in the straps. One end of a piece of string is then looped around the straps. A special stick with a hook at the end is then used to lift the string over the hook. The other end is used by the handicapped person to pull the food item to the level of the freezer compartment. The stick is then used to push the item into the freezer compartment. A tag located on the end of the string now hanging out of the freezer compartment identifies the food item. When the handicapped individual wishes to prepare a meal using a frozen food product, all available food products are within easy view and reach of the individual. With the use of the Assist Handicapped People, no longer is digging and rooting around in a freezer required, where one food item may block the view and access to another.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the Figures.

| LIST OF REFERENCE NUMBERS | | | |
|---|---|---|---|
| 10 | Handicapped Kitchen Aid | 35 | String |
| 20 | Reaching Stick | 40 | Freezer Wall |
| 30 | Bail | | |

1. Detailed Description of the Figures

Figure 1:
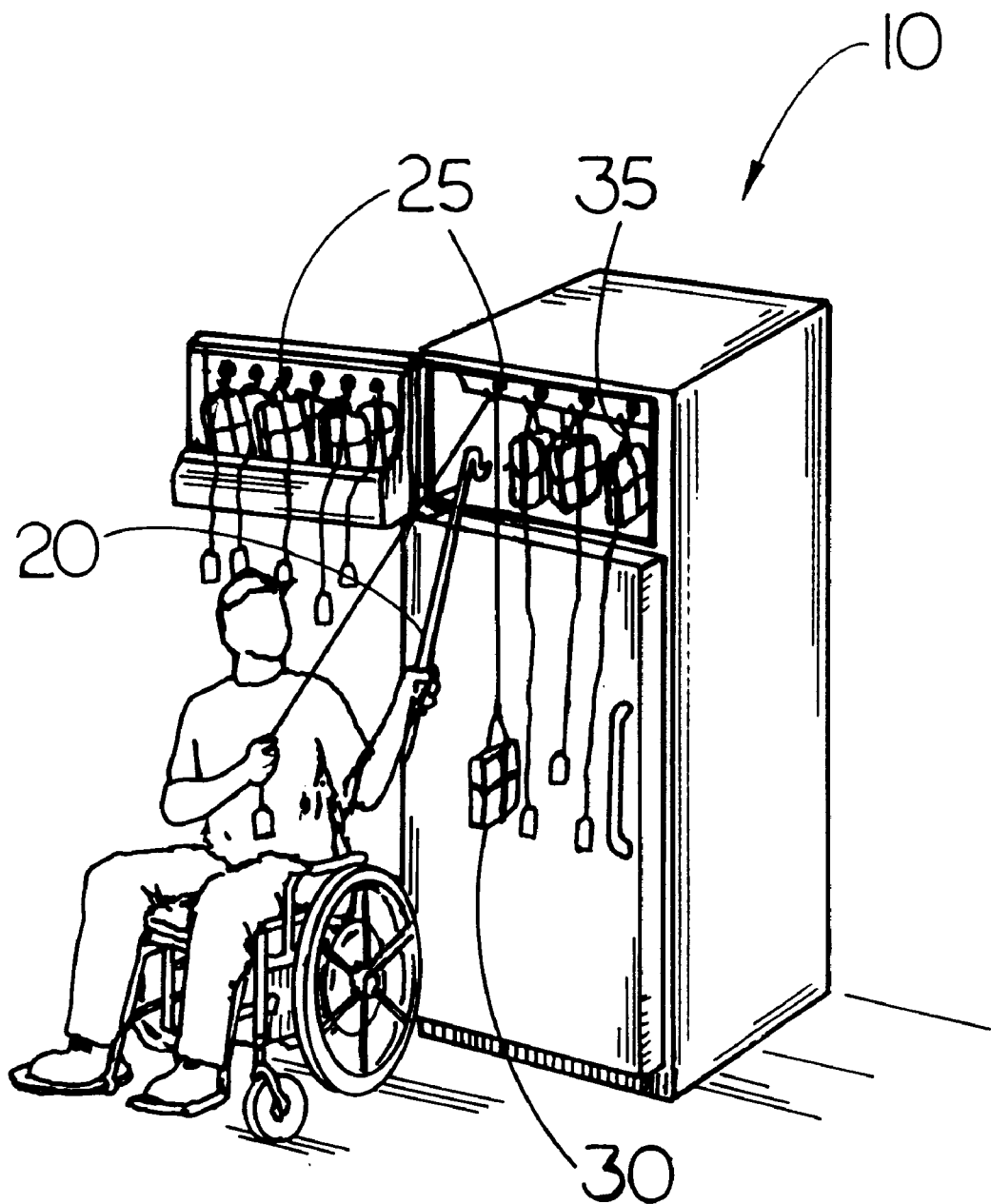
FIG. 1 is a perspective view of a handicapped person in a wheelchair retrieving a food item from a conventional freezer using the method and apparatus for aiding the handicapped for placing and retrieving items, according to the preferred embodiment of the present invention.

Referring now to FIG. 1, a handicapped person in a wheelchair is shown utilizing a reaching stick 20 from a method and apparatus for aiding the handicapped for placing and retrieving items 10 to retrieve a food item from the freezer chest of a conventional upright refrigerator/freezer. The system may be utilized with either prepackaged food items normally found in the supermarket freezer or prepared food placed into a suitable container.

Figure 2:
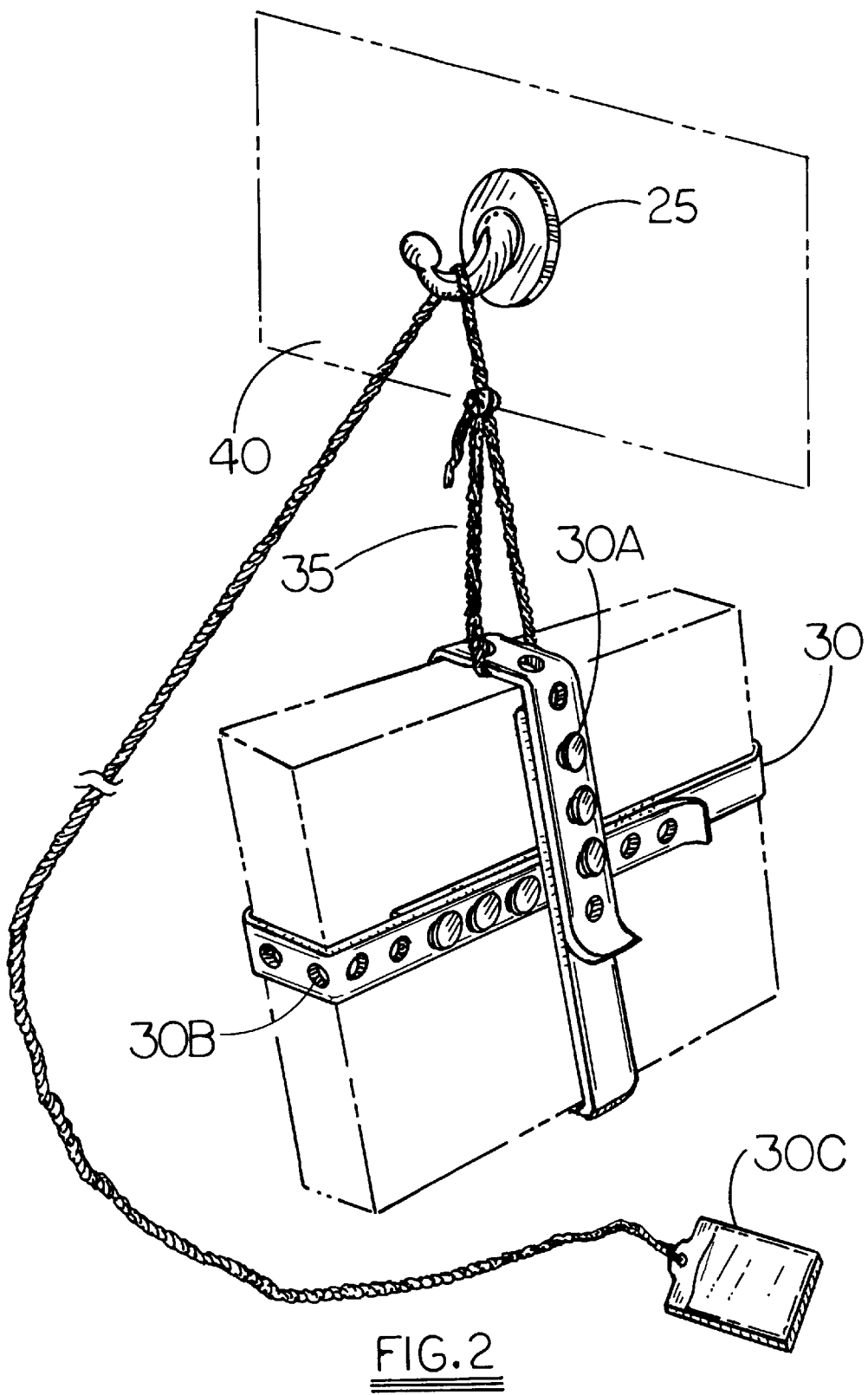
FIG. 2 is a perspective view of a food item in the bundling straps with a piece of string attached to it for pulling the item from a hook permanently attached to a freezer wall using the method and apparatus for aiding the handicapped for placing and retrieving items, according to the preferred embodiment of the present invention.
Figure 3:
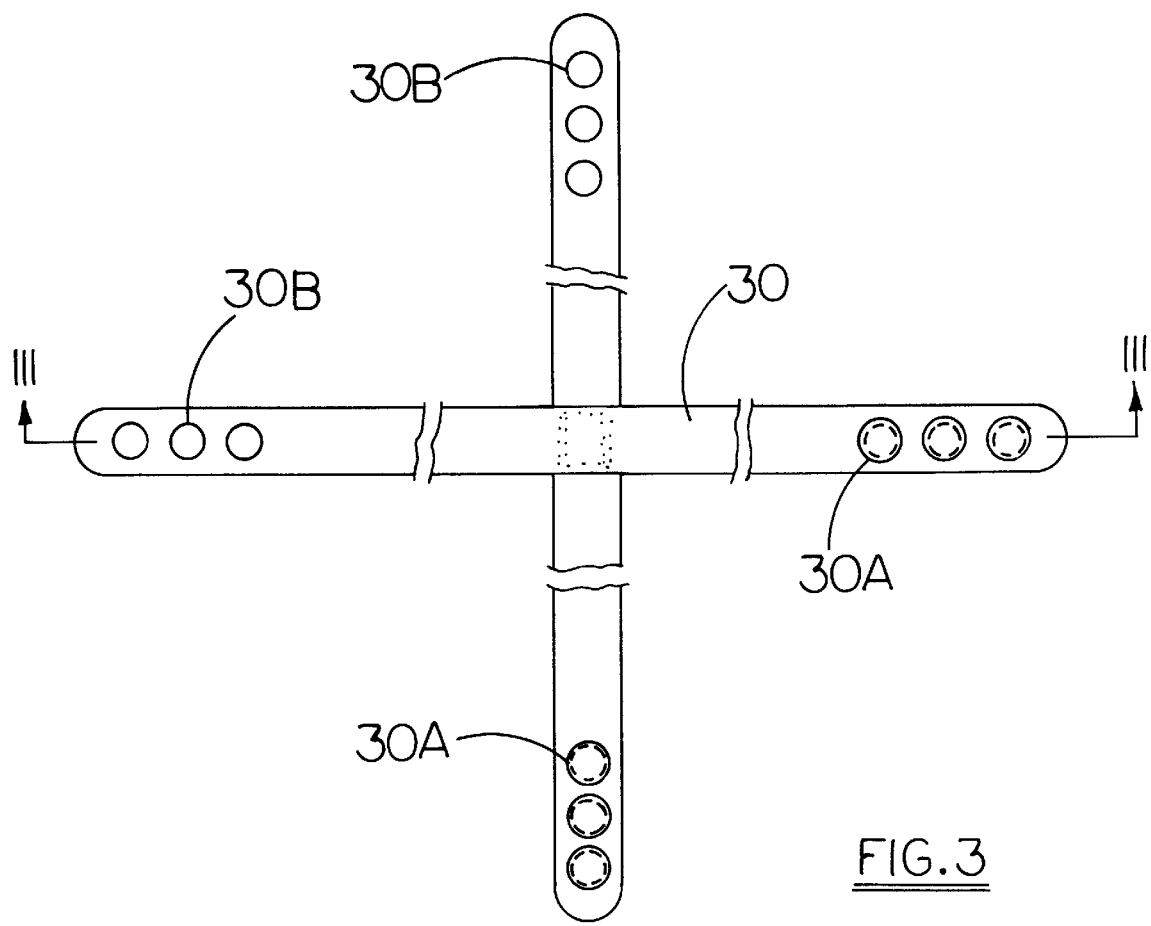
FIG. 3 is a top view of the rubber straps used to band a freezer container and the like as part of the method and apparatus for aiding the handicapped for placing and retrieving items, according to the preferred embodiment of the present invention.

Referring now to FIG. 2, shown is a food container (not part of the disclosure) with string 35 looped around a rubber hook 25 permanently attached to a freezer wall 40. Hook 25 may be attached by an adhesive which is able to withstand the cold temperatures of the freezer compartment. It is envisioned that many such hooks would be supplied in a kit along with the remaining components of the invention. A plurality of hooks 25 may also be permanently attached to a strip which is then attached to freezer wall 40. The user would be able to choose which arrangements of hooks would be most convenient for them. A bail 30 made from two rubber straps is provided for securably wrapping a food container. The straps criss-cross each other in the center and are bonded together via either adhesive or heat. Each of said rubber straps has a plurality of apertures 30b at one end and a plurality of locking tabs 30a at the other. The locking tabs are designed to be pressed through said aperture and retain the two ends of the straps together. In this fashion, the two straps can be wrapped around a food container and then locked together and bind it therein. A piece of string of suitable strength and durability is then attached to this arrangement. The other end of the string is left free to dangle from hook 25. A tag 30c with removable paper inserts, much like luggage tags, is then tied to this free end for identifying the particular food item contained therein. It is important that the tag 30c selected have a clear plastic pouch for inserting a paper inset where the name of the food item can be written thereon. The end of the pouch where the insert is inserted must be oriented upward so the paper insert does not fall out when the tag is hanging from string 35 out of the freezer compartment.

Figure 4:
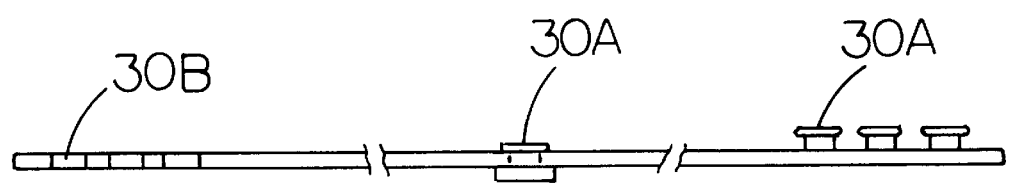
FIG. 4 is a side view of the rubber straps used to band a freezer container and the like as part of the method and apparatus for aiding the handicapped for placing and retrieving items, according to the preferred embodiment of the present invention.

Referring to FIG. 4, shown is a side view of bail 30 showing the detail of locking tabs 30. Locking tabs 30a can be made from any suitable material such as metal, nylon, or plastic. Locking tabs 30a generally are cylindrical with a mushroom head for penetrating an aperture in the straps of bail 30. The stretching rubber will give way around the mushroom head and then retract back around the cylindrical body thereby holding the two ends of the strap together.

Figure 5:
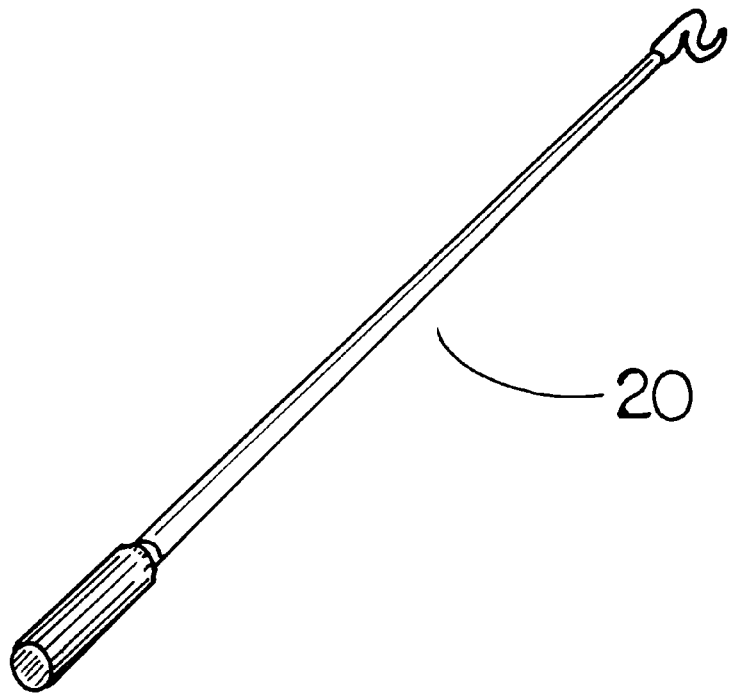
FIG. 5 is a side view of reaching stick used to store and retrieve food items from a freezer as part of the method and apparatus for aiding the handicapped for placing and retrieving items, according to the preferred embodiment of the present invention.

Referring to FIG. 5, shown is a reaching stick 20 for storing and retrieving a food item. Reaching stick 20 is an elongated rod made from plastic, wood, or metal. It has a multi-purpose hook at one end for receiving string 35 and placing it on rubber hook 25. In this fashion, it can be used to both pull and push food items. A wheelchair bound person would need to only lift string 35 to hook 25 with stick 20 and pull on string 35 to lift the food item into the freezer. Stick 20 can then be used to push the food item into place in the freezer compartment.

Figure 6:
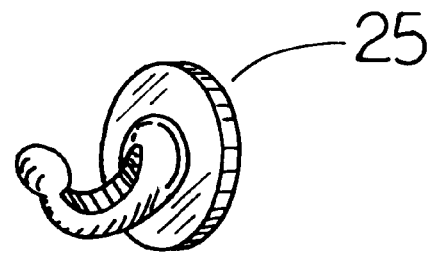
FIG. 6 is a perspective view of a rubber hook used for hanging food items in a freezer as part of the method and apparatus for aiding the handicapped for placing and retrieving items, according to the preferred embodiment of the present invention.

Referring to FIG. 6, shown is a rubber hook 25 used for lifting a food item into a freezer. Rubber hook 25 is typical of hooks found for hanging items having a portion with a member bent for receiving and holding an article attached to a base which is secured to a surface. Rubber hook 25 can be glued to a freezer sidewall or attached with a group of hooks to a strip.

In an alternate preferred embodiment, the method and system to aid the handicapped in placing and retrieving an item 10 can be used to secure and retrieve other articles such as dishes in the kitchen cupboard. It is contemplated that there are many other uses as well and this teaching is meant in no way to be a limitation as such.

2. Operation of the Preferred Embodiment

In operation, a container containing prepackaged foods or home foods are bound by a bail consisting of rubber straps with interlocking tabs. A piece of string is then inserted through this bail and tied off. A handicapped person can then use a special stick with a hook at the end to loop the string around a hook previously installed in the chest of a conventional freezer. The free end of the string dangling from the hook can then be used to pull the food item up to the freezer compartment. The stick can then be used to position the item in the freezer. A tag identifying the food item is tied to the end of the string dangling from the hook and extending out of the freezer compartment. A handicapped person need only choose a food item using the tags, pull slightly on the attached string to lift the food item, use the stick to pull the item out of the freezer compartment, and then lower the item to their lap. In this fashion, a handicapped person can place and retrieve food items from the freezer giving them more independence in caring for themselves.

The foregoing description is included to illustrate the operation of the preferred embodiment and is not meant to limit the scope of the invention. The scope of the invention is to be limited only by the following claims.

What is claimed is:

1. An apparatus and system for aiding the handicapped in placing and retrieving items, consisting of:
   a bail, said bail made from two rubber straps which criss-cross each other in the center and are bonded together via either adhesive or heat for securably wrapping a food container;
   a piece of string, said piece of string having two ends and tied at one end to said bail;
   a tag, said tag secured to the free end of said string for identifying a particular food item in said food container;
   a rubber hook, said rubber hook for placing and retrieving a food item in the freezer;
   a reaching stick, said reaching stick having a multi-purpose hook at one end for placing said string on said rubber hook and for positioning and retrieving a food item from said freezer.

2. The apparatus and system for aiding the handicapped in placing and retrieving items of claim 1, wherein said rubber straps have a plurality of apertures at one end and a plurality of locking tabs at the other designed to be pressed through said aperture and retain the two ends of said straps together.

3. The apparatus and system for aiding the handicapped in placing and retrieving items of claim 2, wherein said locking tabs are generally cylindrical with a mushroom head for penetrating an aperture in said straps of said bail.

4. The apparatus and system for aiding the handicapped in placing and retrieving items of claim 3, wherein said rubber hook has a portion with a member bent for receiving and holding an article attached to a base which is secured to a surface, and wherein said rubber hook can be glued to a freezer wall or attached with a group of hooks to a strip.

5. The apparatus and system for aiding the handicapped in placing and retrieving items of claim 4, wherein said free end of said string is used to pull the food item up to the freezer and said reaching stick is used to position said food item into said freezer.

6. The apparatus and system for aiding the handicapped in placing and retrieving items of claim 4, wherein said free end of said string is used to lower the food item from said freezer.

* * * * *